(12) United States Patent
Dunn

(10) Patent No.: US 12,702,761 B2
(45) Date of Patent: Aug. 11, 2026

(54) LOCKOUT MECHANISM FOR DRUG DELIVERY DEVICE

(71) Applicant: AMGEN INC., Thousand Oaks, CA (US)

(72) Inventor: Andrew Dunn, Santa Monica, CA (US)

(73) Assignee: AMGEN INC., Thousand Oaks, CA (US)

( * ) Notice: Subject to any disclaimer, the term of this patent is extended or adjusted under 35 U.S.C. 154(b) by 774 days.

(21) Appl. No.: 17/779,913

(22) PCT Filed: Nov. 23, 2020

(86) PCT No.: PCT/US2020/061720
§ 371 (c)(1),
(2) Date: May 25, 2022

(87) PCT Pub. No.: WO2021/113101
PCT Pub. Date: Jun. 10, 2021

(65) Prior Publication Data
US 2023/0001099 A1 Jan. 5, 2023

Related U.S. Application Data

(60) Provisional application No. 62/942,607, filed on Dec. 2, 2019.

(51) Int. Cl.
*A61M 5/315* (2006.01)
*A61M 5/32* (2006.01)

(52) U.S. Cl.
CPC ...... *A61M 5/31571* (2013.01); *A61M 5/3202* (2013.01); *A61M 2205/0266* (2013.01); *A61M 2205/3368* (2013.01); *A61M 2205/36* (2013.01)

(58) Field of Classification Search
CPC ............ A61M 5/31571; A61M 5/3202; A61M 2205/0266; A61M 2205/3368
See application file for complete search history.

(56) References Cited

U.S. PATENT DOCUMENTS

2014/0236076 A1 8/2014 Marshall et al.
2018/0339114 A1* 11/2018 Wendland ........... A61M 5/3202

FOREIGN PATENT DOCUMENTS

EP 4257164 A2 * 10/2023 ............ A61M 5/142
WO WO-2016081238 A1 * 5/2016 ........ A61M 5/31571
WO WO-2016/140853 A1 9/2016
WO WO-2018/195270 A1 10/2018

OTHER PUBLICATIONS

International Application No. PCT/US2020/061720, International Search Report and Written Opinion, mailed Mar. 4, 2021.

* cited by examiner

*Primary Examiner* — Bhisma Mehta
*Assistant Examiner* — Haden Matthew Ritchie
(74) *Attorney, Agent, or Firm* — MARSHALL1, GERSTEIN & BORUN LLP

(57) ABSTRACT

A drug delivery device includes a housing, a container at least partially disposed within the housing and configured to contain a medicament, an injection mechanism at least partially disposed within the housing and configured to exert a force to urge the medicament from the container, a drug delivery component at least partially disposed within the housing, and at least one pin positioned adjacent to the housing and preventing activation of the activation mechanism until the at least one pin reaches a desired temperature.

15 Claims, 3 Drawing Sheets

LOCKOUT MECHANISM FOR DRUG DELIVERY DEVICE

CROSS-REFERENCE TO RELATED APPLICATIONS

This is the United States national phase of International Patent Application No. PCT/US2020/061720, filed Nov. 23, 2020, which claims priority to U.S. Provisional Patent Application No. 62/942,607, filed Dec. 2, 2019, the entire contents of each of which are hereby incorporated by reference herein.

FIELD OF DISCLOSURE

The present disclosure generally relates to drug delivery devices and, more particularly, to drug delivery devices having a lockout mechanism for resisting drug delivery until the devices reaches a desired temperature.

BACKGROUND

Drug delivery devices, such as injectors, are used to deliver liquid drugs to a patient. Upon activation, a drug delivery device may expel a drug stored within an internal reservoir of a primary container through a needle, cannula, or other delivery member into the patient. Some drug delivery devices may be temporarily attached to a patient to deliver a drug via an injection needle or some other means over an extended period of time. The drug delivery device may be adhesively attached to the tissue of the patient's abdomen, thigh, arm, or some other portion of the patient's body. Some drug delivery devices may be held against or onto a patient to deliver a drug via an injection needle or some other means over a relatively short period of time.

Many medicaments require refrigeration to maintain stability and performance. Accordingly, it is common for these medicaments to be labeled for cold storage during manufacturing, transportation, and storage processes prior to patient and/or clinician use. These medicaments are often stored at temperatures ranging from approximately 2° C. and approximately 8° C., such as via standard household refrigerators. Cold storage medicaments are often preferably sufficiently warmed prior to administration, such as to reduce or minimize pain and/or to ensure the delivery device functions properly and as intended. Patients may be hesitant to administer these drugs due to warming techniques which may result in risking administering a cold injection or require extended delivery times if the patient fails to wait an appropriate length of time after removing the device from refrigeration. These contributing factors which may extend the time of the perceived injection experience or add discomfort to the user may risk reducing adherence to therapy.

Patients desire both a comfortable and predictable injection experience. Administering injections using devices at substantially similar temperatures often yields substantially similar experiences. Differences of medicament temperatures at the time of administration of approximately 5° C. or more are likely to cause discernible differences to the patient, particularly in medicaments having highly temperature-dependent viscosities, which may lead to hesitation and uncertainty in administering subsequent doses. This in turn may lead to reduced adherence levels.

As described in more detail below, the present disclosure sets forth systems for delivery devices embodying advantageous alternatives to existing systems and methods, and that may address one or more of the challenges or needs mentioned herein, as well as provide other benefits and advantages.

SUMMARY

In accordance with an aspect, a drug delivery device is provided, including: a housing; a container at least partially disposed within the housing, the container configured to contain a medicament; an injection mechanism at least partially disposed within the housing, the injection mechanism configured to exert a force to urge the medicament from the container; a drug delivery component at least partially disposed within the housing; a protective cap selectively coupled with the housing adjacent to the drug delivery component; and a plurality of lock pins positioned adjacent to the housing and the protective cap and preventing relative movement therebetween until the plurality of lock pins reach a desired temperature.

The device may include at least three lock pins annularly spaced about an inner surface of the protective cap. Alternatively, the device may include at least four lock pins annularly spaced about an inner surface of the protective cap.

The housing may include a needle shield at least selectively surrounding the drug delivery component, wherein the plurality of lock pins are each connected to an outer surface of the needle shield. The needle shield may include a plurality of locking notches each configured to selectively engage the plurality of lock pins until the plurality of lock pins reach a desired temperature.

The pins may be shape memory alloys, may be constructed from a bi-metallic material, and/or may be constructed from a nitinol material.

The drug delivery device may include a release component coupled with the housing and configured to selectively permit release of the activation mechanism. The release pin may be positioned adjacent to the housing and the release component to prevent relative movement therebetween, until the at least one release pin reaches a desired temperature.

BRIEF DESCRIPTION OF THE DRAWINGS

The above needs are at least partially met through provision of the temperature indicator for a drug delivery device described in the following detailed description, particularly when studied in conjunction with the drawings, wherein.

The accompanying figures show embodiments according to the disclosure and are exemplary rather than limiting.

Figure 1:
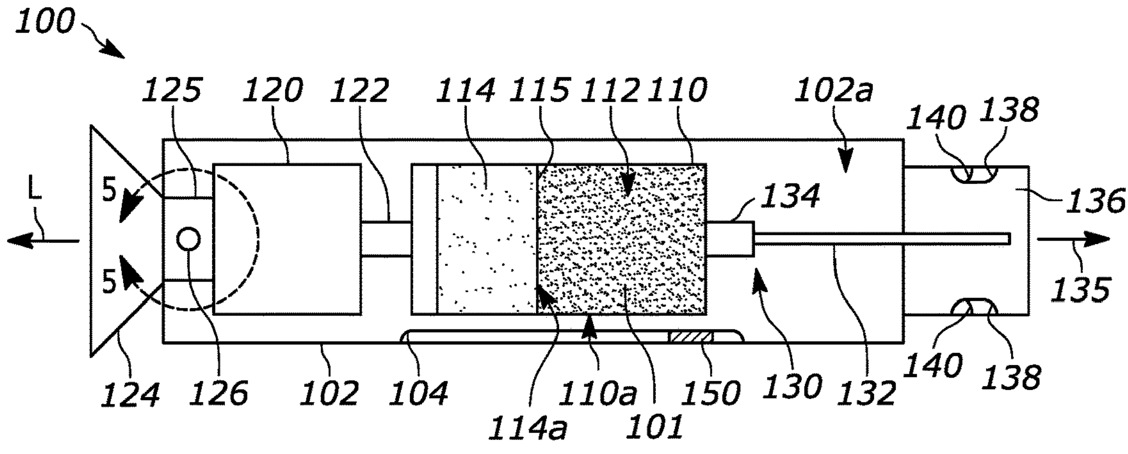
FIG. 1 illustrates a drug delivery device having at least one lockout mechanism for resisting drug delivery until the devices reaches a desired temperature, in accordance with various embodiments.
Figure 2:
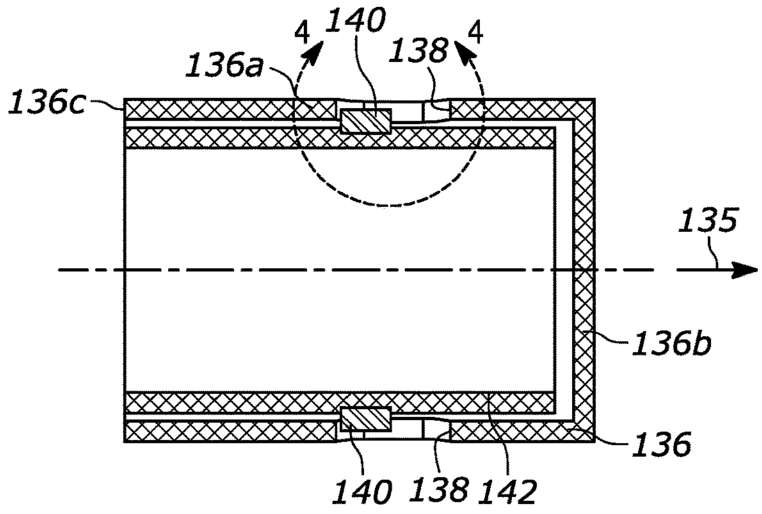
FIG. 2 shows a cross sectional view of an exemplary type of lockout mechanism, which includes a protective cap, in accordance with various embodiments, taken along line A-A in FIG. 3.
Figure 3:
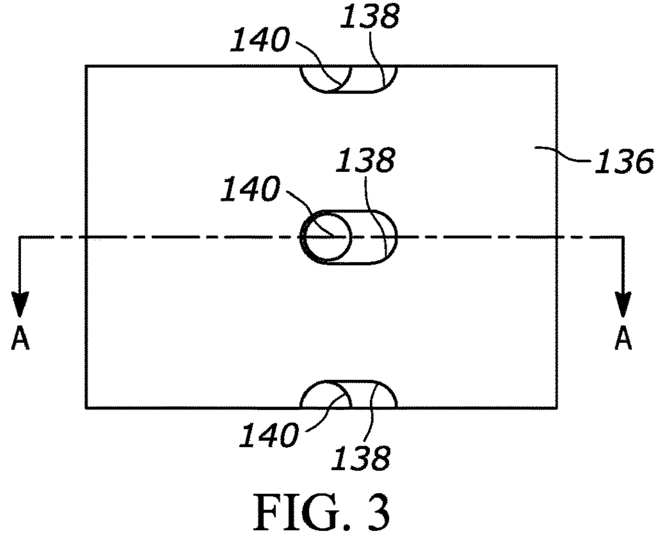
FIG. 3 shows a side view of the exemplary type of lockout mechanism shown in FIG. 2.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a temperature indicator for a drug delivery device that provides lockout mechanism for selectively preventing activation of an injection mechanism until a component of the lockout mechanism has reached a desired temperature, such a suitable temperature for drug administration. Injectable drugs are typically stored in cooling devices such as refrigerators at temperatures ranging between approximately 2° C. to approximately 8° C. Patients are recommended to wait until the drug has increased in temperature before administering the drug to aid in administration comfort. The drug delivery devices, and more specifically, the lockout mechanisms, described herein prevent and/or resist use of the drug delivery devices until the drug has reached a suitable temperature for injection.

Referring to the Figures, a general drug delivery device 100 is provided in the form of an autoinjector having a vertically oriented configuration with some or all drug delivery components disposed in stacked relation along a longitudinal axis L within a housing 102 thereof. As a more specific example, the device 100 can be configured to operate and inject a user with the device 100 oriented generally perpendicular to a skin surface of the user. The drug delivery device 100 can include the aforementioned housing 102 that defines a shell and includes an inner volume 102a and at least one opening 104, a container 110 containing a medicament 101, an injection mechanism 120 for urging the medicament 101 from the container 110, a drug delivery component 132 for delivering the medicament to a patient, a protective cap 136 selectively coupled with the housing 102, a user input mechanism such as an activation button 124 that is depressed by a patient to activate the injection mechanism 120, and a lockout mechanism configured to prevent and/or resist drug delivery until the lockout mechanism reaches a desired temperature. As a more specific example, the lockout mechanism may be a plurality of lock pins 140 positioned adjacent to the housing 102 and the protective cap 136 to prevent relative movement therebetween until the lock pins 140 have reached a desired temperature. As a more specific example, the housing 102 may include a needle shield 142 that is slidably engaged with the main portion of the housing such that the needle shield 142 at least partially surrounds the drug delivery component 132 when it is in a storage position (e.g., non-extended or non-injection position). As another example, the lockout mechanism may be a lock pin 125 positioned adjacent to the housing 102 and the activation button 124 that prevents relative movement therebetween.

The device 100 may also include a needle insertion mechanism 130 for inserting the needle 132 into the user during or just prior to delivery of the medicament. The device 100 may also include a temperature indicator 150 that includes a visual indicator informing a user or health care provider that the device 100 has reached a desired temperature.

In some embodiments, including the one illustrated in FIG. 1, the drug delivery device 100 may be configured as an autoinjector or a pen injector. In other embodiments, the drug delivery device 100 may be in the form of a hybrid handheld device, a wearable drug delivery device such as an on-body injector or an ambulatory infusion pump that may be releasably coupled with a patient, or any other type of handheld devices including hybrids thereof. The drug delivery device 100 may be operated to subcutaneously or transdermally deliver a drug to a patient. The drug delivery device 100 may be configured to automatically deliver a fixed or a patient/operator-settable dose of a drug over a fixed and/or a patient/operator-settable period of time. The drug delivery device 100 may be intended for self-administration by the patient, and in some examples, may be used by a caregiver or a formally trained healthcare provider to administer an injection.

The container 110 includes an outer surface 110a and an interior volume 112. The container 110 (which, in some examples, may be referred to as a primary container) further accommodates a piston 114 within the interior volume 112 thereof. The piston 114 is moveably disposed within the container 110 along the longitudinal axis "L" and has a first end 114a that includes an interior surface 115. The interior surface of the container 110 and the interior surface 115 of the piston 114 define a reservoir to contain a drug or medicament 101. Generally, the at least one opening 104 is aligned with the container 110 to allow a user to see at least a portion of the outer surface 110a of the container 110 for the purposes of completing a visual inspection and/or to determine a quantity of remaining drug and/or medicament 101 prior to, during, and after drug administration.

The volume of the drug 101 contained in the reservoir prior to delivery may be: any volume in a range between approximately (e.g., ±10%) 0.05-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., +10%) 1-3.5 mL, or any volume in a range between approximately (e.g., ±10%) 1-3 mL, or any volume in a range between approximately (e.g., ±10%) 1-2.5 mL, or any volume in a range between approximately (e.g., +10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir may be completely or partially filled with the drug or medicament 101. The drug or medicament 101 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The injection mechanism 120 is coupled to a piston rod 122 to drive the piston 114 through the container 110. The injection mechanism 120 may be in the form of any number of suitable components capable of exerting a force to urge the drug or medicament 101 out of the container 110. In some examples, the injection mechanism 120 may include a user input device 124 such as, for example, the button 124, that may be engageable by a user to initiate drug delivery.

The needle insertion mechanism 130 is operably coupled with the injection mechanism 120 to insert a needle and/or a cannula 132 to deliver the drug or medicament 101. More specifically, the needle insertion mechanism 130 includes the needle and/or cannula 132 oriented along the longitudinal axis L, a flow path 134 fluidly coupling the reservoir to the needle and/or cannula 132, a protective cap 136 configured to selectively and at least partially surround the needle and/or cannula 132 to reduce the likelihood and/or prevent unintentional needle sticks and to reduce and/or prevent contamination of the needle and/or cannula 132. For example, the protective cap 136 may include an annular portion **136*a* that substantially or completely surrounds the sides of the needle and/or cannula 132. The protective cap 136 may also include an end face 136*b* that cooperates with the annular portion 136*a* to substantially or completely enclose the portion of the needle and/or cannula 132 that extends past the housing 102 when the needle and/or cannula 132 is in a storage position (as shown in FIG. 1). As a more specific example, protective cap 136 may be selectively coupled with the needle shield 142 when the device 100 is in the storage configuration (as shown in FIG. 1). As an even more specific example, the protective cap 136 may surround the outer surface of the needle shield 142 such as to form a closed or substantially closed environment within the needle shield 142. In such a configuration, the protective cap 136 annular portion 136*a* may have an inner diameter that is at least slightly larger than the outer diameter of the needle shield 142 to facilitate removal of the protective cap 136 when desired (e.g., prior to injection). Additionally or alternatively, the protective cap 136 may be received within the inner surface of the needle shield 142 such as to form a closed or substantially closed environment within the needle shield 142. In such a configuration, the protective cap 136 may have an annular portion 136*a* that has an outer diameter that is at least slightly smaller than the inner diameter of the needle shield 142 and/or an end face 136*b* that has a larger diameter than both the annular portion 136*a* and the needle shield 142 such that the protective cap end face 136*b* extends radially outwardly to further seal the environment within the needle shield 142 and/or to improve user grip when removing the protective cap 136. As a more specific example, the protective cap is removed by pulling or otherwise urging it in direction 135 (a.k.a. the distal direction) so that the needle shield 142** is no longer covered.

The needle shield 142 may be configured to activate and/or permit the device to activate. For example, the needle shield 142 may have extension arms (not shown) or other suitable components to act on and/or actuate the injection mechanism 120. Additionally or alternatively, the needle shield 142 may act on and/or actuate a component that permits the device to be activated but does not actually do so; for example the movement of the needle shield 142 in the proximal direction (e.g., in the opposite direction of direction 135) may unlock a component thereby allowing depression of the button 124, which in turn actuates the injection mechanism 120. In some examples, the injection mechanism 120 may be configured to drive both movement of the piston 114 and the needle and/or cannula 132 by moving any combination of the container 110, the flow path 134, and/or the needle and/or cannula 132. As commonly configured, one or more of the components of the device 100, such as the drive mechanism 108 and needle insertion mechanism 116, can be operable in response to actuation of a user input device 124 which is accessible on an exterior of the housing 102. Suitable activation mechanisms 120 include, but are not limited to, springs, gas sources, phase changing materials, motors, or other electromechanical systems. As previously noted, the controller 126 may control operation of one or more of the drug delivery components.

The protective cap 136 may be configured to prevent or resist movement of the needle shield 142 while the protective cap 136 is in place. For example, the distal end **136*c* of the protective cap 136 may abut against a portion of the housing 102 or another component of the device 100 thereby preventing movement of the needle shield 142** in the proximal direction.

As indicated above, the device 100 includes at least one lockout mechanism configured to prevent and/or resist drug delivery until the lockout mechanism reaches a desired temperature. One exemplary lockout mechanism is the plurality of lock pins 140 positioned adjacent to the housing 102 and the protective cap 136 to prevent relative movement therebetween until the lock pins 140 have reached a desired temperature. As a more specific example, the lock pins 140 are made of a shape memory alloy (commonly known as nitinol) or other suitable materials that, once shape set during manufacture, return to their original shape only when warmed. The materials may be customized to activate and return to their original shape within a certain temperature range, such as by utilizing parameters in the below table:

Nitinol Transformation Properties

| Common Name * | Ingot A(p) | Active A(f) * | Description |
|---|---|---|---|
| N | −20 C. to −5 C. | 0 C. to 20 C. | High Nickel Super Elastic Nitinol |
| S | −5 C. to 15 C. | 10 C. to 20 C. | Super Elastic Nitinol |
| C | −20 C. to −5 C. | 0 C. to 10 C. | Chromium Doped Super Elastic Nitinol |
| B | 15 C. to 45 C. | 20 C. to 40 C. | Body Temperature Nitinol |
| M | 45 C. to 95 C. | 45 C. to 95 C. | Mid Temperature Range Nitinol |
| H | >95 C. | 95 C. to 115 C. | High Temperature Range Nitinol |

Figure 4A:
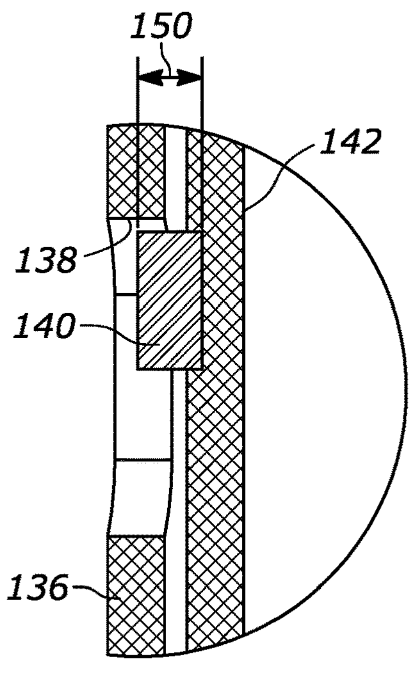
FIGS. 4*a* and 4*b* show cross sectional views of the lockout mechanism shown in FIG. 2, along line 4-4 in FIG. 2.
Figure 4B:
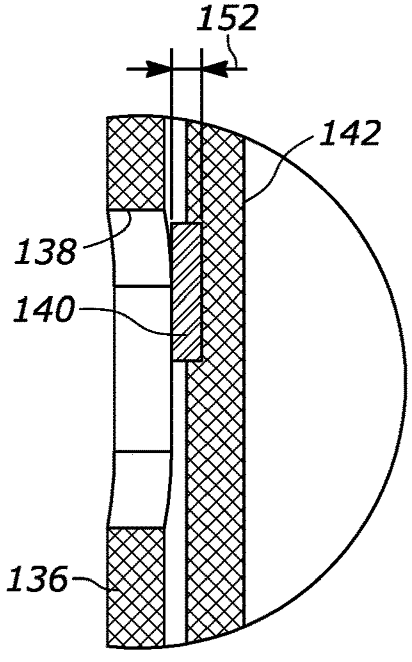

For example, these properties can be utilized to design a feature within the device 100 that prevents and/or resists the user from removing the protective cap 136, depressing the button 124, and/or otherwise activating the device 100 until the designed desired use temperature has been reached. As a more specific example, as shown in FIGS. 2, 3, 4*a* and 4*b*, the lock pins 140 are coupled with at least one of the protective cap 136 and the needle shield 142 to prevent relative movement therebetween. In the figures, the lock pins 140 are coupled with the needle shield 142 and aligned with slots 138 in the protective cap 136 such that the lock pins 140 abut the slots 138 when the lock pins 140 are below the desired temperature (FIG. 4*a*) and do not abut the slots 138 when the lock pins 140 are above the desired temperature (FIG. 4*b*). For example, as shown in FIG. 4*a*, the lock pins 140 each have a thickness 150 when they are at a temperature that is below the desired temperature; at this thickness 150 the lock pins 140 engage the slots 138 of the protective cap 136 and prevent and/or resist relative movement between the needle shield 142 and the protective cap 136. As a more specific example, at this thickness 150 the lock pins 140 may permit some relative movement but still prevent and/or resist removal of the protective cap 136 from the needle shield 142 and/or other components of the housing. As shown in FIG. 4*b*, the lock pins 140 each have a thickness 152 when they are at a temperature that is above the desired temperature; at this thickness 152 the lock pins 140 do not engage the slots 138 of the protective cap 136 and do not prevent and/or resist relative movement between the needle shield 142 and the protective cap 136.

During use, when the device is relatively cold, the lock pins 140 are in their expanded (relatively thick) shape geometry and generally prevent the user from removing the protective cap 136. When the device 100 is removed from cold storage and warms to the designed alloy transition temperature, the lock pins 140 get smaller in thickness until they are small enough to clear the slots 138. With the lock pins 140 out of the way, the user can remove the protective cap 136 along the direction 135. With this configuration, a user and/or health care provider may be prevented or discouraged from removing the protective cap 136 until the device 100 has reached a temperature suitable for injection, thereby potentially preventing and/or reducing instances of too-cold injection (which may cause discomfort and/or undesirable drug efficacy issues) and potentially reducing the time that the needle is exposed to outside conditions (potentially leading to breach of cleanliness/sterility).

As discussed above, the device 100 may also include an indicator 150 to alert the user when the device 100 has reached a suitable and/or desirable temperature for injection. For example, the temperature indicator 150 may be in the form of a liquid crystal and/or a leuco dye member that is thermally coupled with the outer surface 110*a* of the container 110. In some examples, the temperature indicator 150 may be in the form of a disc member that is affixed and/or adhered directly to the outer surface 110*a* of the container 110. In other examples, the temperature indicator 150 may be in the form of a label, strip, or painted component affixed to the container 110. The temperature indicator 150 may be constructed from a material having high thermal conductivity and elastomeric properties so that close physical contact with the container 110 provides for high thermal responsiveness.

In some examples, the temperature indicator 150 may be responsive to a designated temperature range such as, for example, between an administration temperature of approximately 15° C. and approximately 35° C., and preferably between approximately 22° C. and approximately 28° C. Other examples of suitable temperature ranges are possible. In some examples, the temperature indicator 150 may be a first color and/or pattern (e.g., generally clear) when exposed to a low temperature, and may shift to a second color and/or pattern (e.g., green) when being exposed to a higher temperature suitable for drug administration. In some examples, the temperature indicator 150 may change colors in a reversed manner. The temperature indicator 150 may be coupled with and positioned on the outer surface 110*a* of the container. The temperature indicator 150 in FIG. 1 is positioned with the opening 104 so that a user may look through the opening 104 to discern the color of the temperature indicator 150 (as well as to observe whether the drug or medicament 101 includes any particulates, discoloration, and/or abnormalities), and thus whether the drug or medicament 101 is at a suitable administration temperature. Such a configuration advantageously provides close proximity with the drug or medicament 101. More specifically, because the temperature indicator 150 is thermally coupled with the container 110, when the container 110 increases in temperature due to being removed from the refrigeration unit, the temperature indicator 150 will reflect the increase in temperature by changing colors.

The device 100 may have any suitable number of lock pins 140, such as one, two, three, four, or more than four. In the instance where the device includes more than one lock pins 140, they may be evenly spaced apart from each other along the circumference of the needle shield 142 and/or the protective cap 136. For example, if the device includes four lock pins 140, they may be spaced apart from each other by approximately 90 degrees. The lock pins 140 may have any suitable shape, such as a round button shaped component as shown in FIG. 1. Additionally, the device may include a lock ring (not shown) instead of or in addition to the lock pins 140 that expands or constricts based on temperature. The ring may be coupled with at least one of the needle shield 142 and/or the protective cap 136. The lock pins 140 and/or the lock ring may be coupled to the needle shield 142 (and/or the protective cap 136) by any suitable configuration, such as an adhesive, by heat-melting the lock pins 140 or lock ring into the needle shield 142, and/or by inserting the lock pins 140 or lock ring into a corresponding-shaped indentation in the needle shield 142.

The device 100 may also include a label or a tag, such as a tag connected to the protective cap 136 that indicates to the user that the protective cap 136 will remain locked until the device 100 has reached the desirable temperature. For example, the tag may read, "CAP WILL REMAIN LOCKED DURING COLD STORAGE" or "CAP WILL REMAIN LOCKED UNTIL REACHING SUITABLE INJECTION TEMPERATURE."

Figure 5A:
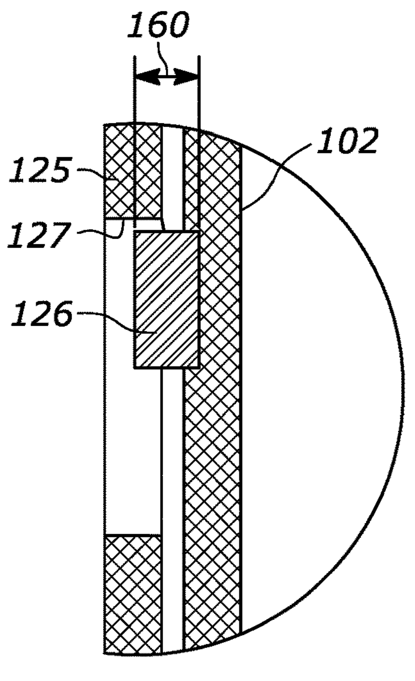
FIGS. 5*a* and 5*b* show cross sectional views of another exemplary type of lockout mechanism, which includes a user input device, in accordance with various embodiments, taken along line 5-5 in FIG. 1.
Figure 5B:
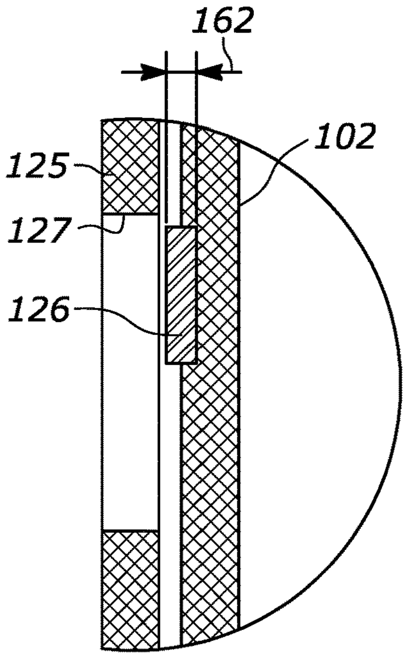

As discussed above, the device 100 may additionally or alternatively include a lock out mechanism associated with the button 124, such as the internal activation mechanism within the device or an external surface of the button 124. For example, the shape memory alloy pins 126 may be installed into the device 100 where components must move relative to one another to activate the injection sequence. When the device 100 is cold, the pins 126 are too long to allow the mechanism to move and start the injection sequence. When the device reaches the shape memory alloy transition temperature, the pins 126 clear the mechanism and allow the injection to be activated by the user. As a more specific example shown in FIGS. 1, 5*a*, and 5*b*, the device 100 may include an extender ring 125 coupled with the button 124 (or integrally formed with the button 124) for acting on the injection mechanism 120 and triggering a drug injection. For example, the pins 126 are coupled with at least one of the housing 102 and the extender ring 125 to prevent relative movement between the same. In the figures, the lock pins 126 are coupled with the housing 102 and aligned with slots 127 in the extender ring 125 such that the lock pins 126 abut the slots 127 when the lock pins 126 are below the desired temperature (FIG. 5*a*) and do not abut the slots 127 when the lock pins 126 are above the desired temperature (FIG. 5*b*). For example, as shown in FIG. 5*a*, the lock pins 126 each have a thickness 160 when they are at a temperature that is below the desired temperature; at this thickness 160 the lock pins 126 engage the slots 127 of the extender ring 125 and prevent and/or resist relative movement between the extender ring 125 and the housing 102. As a more specific example, at this thickness 160 the lock pins 126 may permit some relative movement but still prevent and/or resist depression of the button 124 to a distance sufficient to activate the device 100 injection sequence. As shown in FIG. 5*b*, the lock pins 126 each have a thickness 162 when they are at a temperature that is above the desired temperature; at this thickness 162 the lock pins 126 do not engage the slots 127 of the extender ring 125 and do not prevent and/or resist relative movement between the button 124 and the housing 102.

During use, when the device is relatively cold, the lock pins 126 are in their expanded (relatively thick) shape geometry and generally prevent the user from depressing the button 124 by a distance sufficient to activate the device 100 injection sequence. When the device 100 is removed from cold storage and warms to the designed alloy transition temperature, the lock pins 126 get smaller in thickness until they are small enough to clear the slots 127. With the lock pins 126 out of the way, the user can depress the button 124 along the direction 135. With this configuration, a user and/or health care provider may be prevented or discouraged from depressing the button 124 until the device 100 has reached a temperature suitable for injection, thereby potentially preventing and/or reducing instances of too-cold injection (which may cause discomfort and/or undesirable drug efficacy issues) and potentially reducing the time that the needle is exposed to outside conditions (potentially leading to breach of cleanliness/sterility).

The device 100 may have any suitable number of lock pins 126, such as one, two, three, four, or more than four. In the instance where the device includes more than one lock pins 126, they may be evenly spaced apart from each other along the circumference of the extender ring 125 and/or housing 102. For example, if the device includes four lock pins 126, they may be spaced apart from each other by approximately 90 degrees. The lock pins 126 may have any suitable shape, such as a round button shaped component as shown in FIG. 1. Additionally, the device may include a lock ring (not shown) instead of or in addition to the lock pins 126 that expands or constricts based on temperature. The ring may be coupled with at least one of the housing 102 and/or the extender ring 125. The lock pins 126 and/or the lock ring may be coupled to the housing 102 (and/or the extender ring 125) by any suitable configuration, such as an adhesive, by heat-melting the lock pins 126 or lock ring into the housing 102, and/or by inserting the lock pins 126 or lock ring into a corresponding-shaped indentation in the housing 102.

The device 100 may also include a label or a tag, such as a tag connected to the device adjacent to the button 124 that indicates to the user that the button 124 will remain locked until the device 100 has reached the desirable temperature. For example, the tag may read, "BUTTON MAY NOT BE DEPRESSED DURING COLD STORAGE" or "BUTTON MAY NOT BE DEPRESSED UNTIL REACHING SUITABLE INJECTION TEMPERATURE."

Figure 6A:
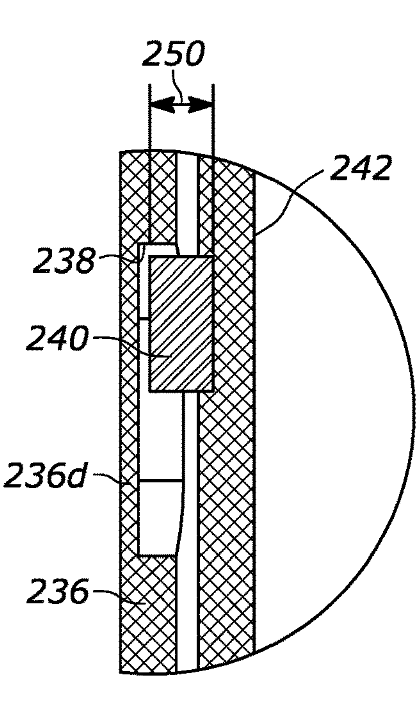
FIGS. 6a and 6b show cross sectional views, similar to those in FIGS. 4a and 4b, of an alternative drug delivery device having at least one lockout mechanism for resisting drug delivery until the devices reaches a desired temperature, in accordance with various embodiments.
Figure 6B:
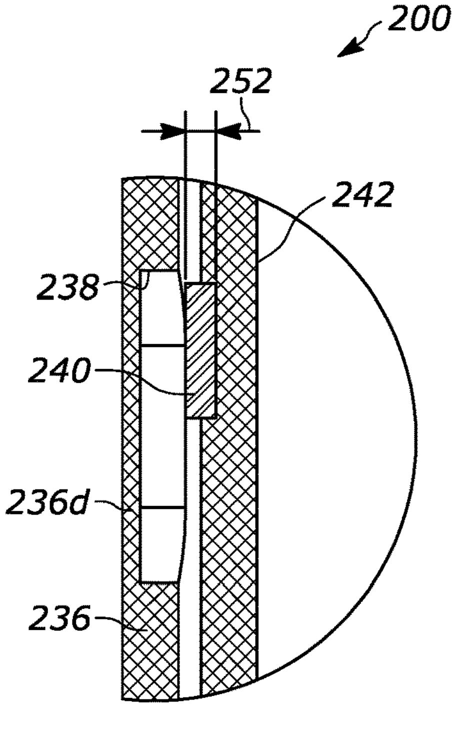

Referring to FIGS. 6*a* and 6*b*, an alternative embodiment is shown, where the device 200 includes lock pins 240 that are coupled with at least one of a protective cap 236 and a needle shield 242 to prevent relative movement therebetween. In FIGS. 6*a*-6*b*, the lock pins 240 are coupled with the needle shield 242 and aligned with slots 238 in the protective cap 236 such that the lock pins 240 abut the slots 238 when the lock pins 240 are below the desired temperature (FIG. 6*a*) and do not abut the slots 238 when the lock pins 240 are above the desired temperature (FIG. 6*b*). For example, as shown in FIG. 6*a*, the lock pins 240 each have a thickness 250 when they are at a temperature that is below the desired temperature; at this thickness 250 the lock pins 240 engage the slots 238 of the protective cap 236 and prevent and/or resist relative movement between the needle shield 242 and the protective cap 236. As a more specific example, at this thickness 250 the lock pins 240 may permit some relative movement but still prevent and/or resist removal of the protective cap 236 from the needle shield 242 and/or other components of the housing. As shown in FIG. 6*b*, the lock pins 240 each have a thickness 252 when they are at a temperature that is above the desired temperature; at this thickness 252 the lock pins 240 do not engage the slots 238 of the protective cap 236 and do not prevent and/or resist relative movement between the needle shield 242 and the protective cap 236. The protective cap 236 shown in FIGS. 6*a* and 6*b* include a wall 236*d* generally aligned with the slot 238 such that the exterior surface of the protective cap 236 forms a complete or substantially complete boundary around the needle shield 242 and/or so the lock pins 240 are not visible by the user when the protective cap 236 is in the storage configuration. It may be desirable to utilize the embodiment in FIGS. 6*a*-6*b* to prevent or reduce the chance of air or outside contaminants from entering the area surrounding the needle. However, it may also or alternatively be desirable to utilize the embodiment in FIGS. 4*a*-4*b* so a user is able to see the lock pins and understand their purpose and/or the locked state of the device 100.

The device may also utilize shape memory alloys could be fabricated into actuators (muscle wires) that move locking features for the cap and/or device activation mechanisms. Using the materials to create actuators could allow for more robust, complex, or low-cost locking mechanisms by allowing for stronger or cheaper materials to be used to create the lock while the shape memory alloy is only used to release the locks once the desired temperature has been reached. Locking features of varying complexity could be designed without being constrained by the fabrication limitations of shape memory alloys.

Figure 7A:
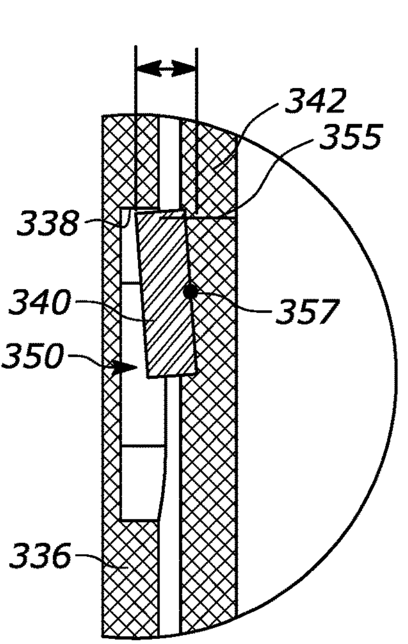
FIGS. 7a and 7b show cross sectional views, similar to those in FIGS. 4a and 4b, of an alternative drug delivery device having at least one lockout mechanism for resisting drug delivery until the devices reaches a desired temperature, in accordance with various embodiments.
Figure 7B:
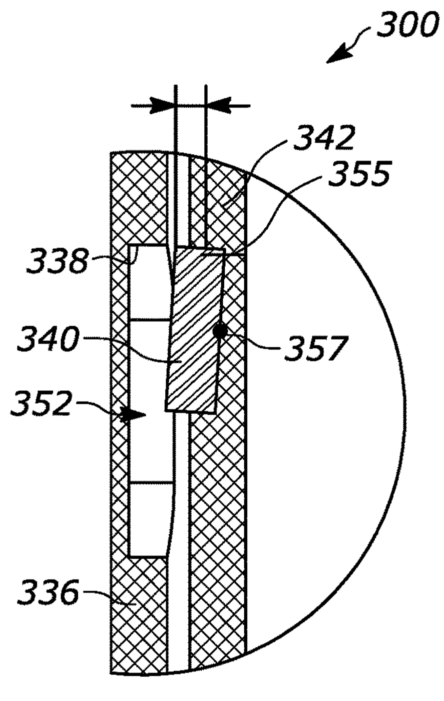

For example, referring to FIGS. 7*a* and 7*b*, an exemplary embodiment is shown utilizing actuators. For example, the device 300 includes lock arms 340 that are coupled with at least one of a protective cap 336 and a needle shield 342 to prevent relative movement therebetween. In FIGS. 7*a*-7*b*, the lock arms 340 are coupled with the needle shield 342 and aligned with slots 338 in the protective cap 336 such that the lock arms 340 abut the slots 338 when the lock arms 340 are below the desired temperature (FIG. 7*a*) and do not abut the slots 338 when the lock arms 340 are above the desired temperature (FIG. 7*b*). For example, as shown in FIG. 7*a*, the lock arms 340 are connected to a shape wire 355 and are pivotable about a pivot pin 357 such that the lock arms 340 each have a first position 350 when the shape wire 355 is at a temperature that is below the desired temperature; at this position 350 the lock arms 340 engage the slots 338 of the protective cap 336 and prevent and/or resist relative movement between the needle shield 342 and the protective cap 336. As a more specific example, at this position 350 the lock arms 340 may permit some relative movement but still prevent and/or resist removal of the protective cap 336 from the needle shield 342 and/or other components of the housing. As shown in FIG. 7*b*, the lock arms 340 each have a position 352 when the shape wire 355 is at a temperature that is above the desired temperature; at this position 352 the lock arms 340 do not engage the slots 338 of the protective cap 336 and do not prevent and/or resist relative movement between the needle shield 342 and the protective cap 336.

The device 300 may have any suitable number of lock arms 340, such as one, two, three, four, or more than four. In the instance where the device includes more than one lock arms 340, they may be evenly spaced apart from each other along the circumference of the needle shield 342 and/or the protective cap 326. The lock arms 340 may have any suitable shape. Additionally or alternatively, the device 300 may utilize at least one lock arm and actuator (e.g., muscle wire) to selectively prevent an actuator button (such as button 124) until the device has reached a desired temperature.

It will be understood that although FIG. 1 shows the components centered along the longitudinal axis L, one or more of the components can be disposed off-center from the longitudinal axis L within the housing 102 and still be considered to be in a stacked relation. In one example, an autoinjector drug delivery device having drug delivery components in a stacked relation corresponds to the container 110 co-axially aligned with the needle and/or cannula 132. Examples of suitable autoinjector devices are described in U.S. Ser. No. 62/447,174, filed Jan. 17, 2017, which is hereby incorporated by reference herein.

It is appreciated that the drug delivery devices and lock out mechanisms may include any number of suitable alternatives.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Rα mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA) x anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1 x IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33 x anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3) x anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP x 4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19 x CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3 x epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33 x anti-CD3 BiTE® (bispecific T cell engager) construct. In some embodiments, the drug delivery device may contain or be used with AMG 701 or another product containing a half-life extended (HLE) anti-B-cell maturation antigen (BCMA) x anti-CD3 BiTE® (bispecific T cell engager) construct. In some embodiments, the drug delivery device may contain or be used with AMG 757 or another product containing a half-life extended (HLE) anti-delta-like ligand 3 (DLL3) x anti-CD3 BiTE® (bispecific T cell engager) construct. In some embodiments, the drug delivery device may contain or be used with AMG 910 or another product containing a half-life extended (HLE) epithelial cell tight junction protein claudin 18.2 x CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:

a housing having a longitudinal axis;

a container at least partially disposed within the housing, the container configured to contain a medicament;

an injection mechanism at least partially disposed within the housing, the injection mechanism configured to exert a force to urge the medicament from the container;

a drug delivery component at least partially disposed within the housing;

a protective cap selectively coupled with the housing adjacent to the drug delivery component; and a plurality of lock pins positioned next to the housing and the protective cap and preventing relative movement therebetween until the plurality of lock pins reach a desired temperature, the plurality of lock pins each having a first thickness at a temperature below the desired temperature for activation of the injection mechanism and a second thickness at the desired temperature, a change between the first thickness and the second thickness enabling activation of the injection mechanism without displacement of the plurality of lock pins relative to the longitudinal axis.

2. The drug delivery device of claim 1, wherein the plurality of lock pins includes at least three lock pins annularly spaced about an inner surface of the protective cap.

3. The drug delivery device of claim 2, wherein the plurality of lock pins includes at least four lock pins annularly spaced about the inner surface of the protective cap.

4. The drug delivery device of claim 1, wherein the housing includes a needle shield at least selectively surrounding the drug delivery component, wherein the plurality of lock pins are each connected to an outer surface of the needle shield.

5. The drug delivery device of claim 4, wherein the needle shield includes a plurality of locking notches each configured to selectively engage the plurality of lock pins until the plurality of lock pins reach the desired temperature.

6. The drug delivery device of claim 1, wherein the plurality of lock pins are shape memory alloys.

7. The drug delivery device of claim 1, wherein the plurality of lock pins are constructed from a bi-metallic material.

8. The drug delivery device of claim 1, wherein the plurality of lock pins are constructed from a nitinol material.

9. The drug delivery device of claim 1, further comprising a release component coupled with the housing and configured to selectively permit release of the injection mechanism; and at least one release pin positioned adjacent to the housing and the release component and preventing relative movement therebetween until the at least one release pin reaches the desired temperature.

10. A drug delivery device comprising:

a housing having a longitudinal axis;

a container at least partially disposed within the housing, the container configured to contain a medicament;

an injection mechanism at least partially disposed within the housing, the injection mechanism configured to exert a force to urge the medicament from the container;

a drug delivery component at least partially disposed within the housing;

a release component coupled with the housing and configured to selectively permit release of the injection mechanism; and at least one release pin positioned next to the housing and the release component and preventing relative movement therebetween until the at least one release pin reaches a desired temperature, the at least one release pin having a first thickness at a temperature below the desired temperature for activation of the injection mechanism and a second thickness at the desired temperature, a change between the first thickness and the second thickness enabling activation of the injection mechanism without displacement of the at least one release pin relative to the longitudinal axis.

11. The drug delivery device of claim 10, wherein the at least one release pin contains shape memory alloys.

12. The drug delivery device of claim 10, wherein the at least one release pin is constructed from a bi-metallic material.

13. The drug delivery device of claim 10, wherein the at least one release pin is constructed from a nitinol material.

14. A drug delivery device comprising:

a housing having a longitudinal axis;

a container at least partially disposed within the housing, the container configured to contain a medicament;

an injection mechanism at least partially disposed within the housing, the injection mechanism configured to exert a force to urge the medicament from the container;

a drug delivery component at least partially disposed within the housing; and at least one lock out mechanism positioned next to the housing and preventing activation of the injection mechanism until the at least one lock out mechanism reaches a desired temperature, the at least one lock out mechanism having a first thickness at a temperature below the desired temperature for activation of the injection mechanism and a second thickness at the desired temperature, a change between the first thickness and the second thickness enabling activation of the injection mechanism without displacement of the at least one lock out mechanism relative to the longitudinal axis occurring during the change between the first thickness and the second thickness.

15. The drug delivery device of claim 14, wherein the at least one lock out mechanism contains a shape memory alloy.

* * * * *